United States Patent [19]
Foresta et al.

[11] Patent Number: 5,637,614
[45] Date of Patent: Jun. 10, 1997

[54] 6,7-DISUBSTITUTED-2-AMINOTETRALINES AND PHARMACEUTICAL COMPOSITIONS CONTAINING THE SAME

[75] Inventors: Piero Foresta, Pomezia; Mauro Marzi; Maria O. Tinti, both of Rome, all of Italy

[73] Assignee: Sigma Tau, Pomezia, Italy

[21] Appl. No.: 639,431

[22] Filed: Apr. 29, 1996

Related U.S. Application Data

[63] Continuation of Ser. No. 714,851, Jun. 13, 1991, abandoned.

[30] Foreign Application Priority Data

Jun. 15, 1990 [IT] Italy ............................... 48066A/90

[51] Int. Cl.$^6$ .......................... A61K 31/225; C07C 69/00
[52] U.S. Cl. ............................. 514/548; 560/141
[58] Field of Search ................... 514/647, 547, 514/548; 560/141

[56] References Cited

U.S. PATENT DOCUMENTS 4,593,042  6/1986  Liang ........................ 514/523

OTHER PUBLICATIONS

Atwal et al "Substituted 1,2,3,4 Tetra Hydroaminonaphthols Anti Hypertensive Agents, Calcium Channel Blockers and Adrenergic Receptor Blockers With Calecholamine–Depleting Effects" *J. Med. Chem.* 30:627–635 (1987).

Ertel et al "Immunoprotective Effect of Calcium Channel Blocker on Macrophage Antigen Presentation Function, Major Histocompatability Class II Antigen . . . " Surgery 108:154–160 (1990).

*Primary Examiner*—Raymond Henley, III
*Attorney, Agent, or Firm*—McDonnel Boehnen Hulbert & Berghoff

[57] ABSTRACT

6,7-disubstituted-2-aminotetralines of general formula (1)

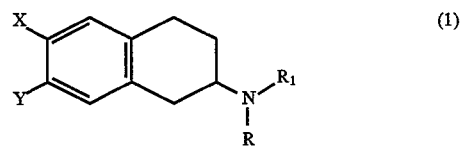

and their pharmacologically acceptable salts, wherein X and Y, identical or different are selected from the group consisting of methoxy, acetoxy and fluoro; and R and $R_1$, identical or different, are selected from the group consisting of hydrogen, ethyl, propyl, cyclopropylmethyl, 2-hydroxy-2-phenylethyl, 2-hydroxy-2-(4-methylphenyl)ethyl and 2-hydroxy-3-(4-methoxyphenoxy)propyl are endowed with immunomodulator activity.

2 Claims, No Drawings

6,7-DISUBSTITUTED-2-AMINOTETRALINES AND PHARMACEUTICAL COMPOSITIONS CONTAINING THE SAME

This application is a continuation of application Ser. No. 07/714,851 filed Jun. 13, 1991, now abandoned.

BACKGROUND OF THE INVENTION

1. Field of the Invention

This invention is in the field of pharmaceutical compositions active as immunomodulators and methods for immunomodulation.

2. Prior Art Disclosure

Of Compounds (1)–(6), the compounds (1)–(5) are already known; in particular, the compounds ST 563 and ST 570 are disclosed in the European patent publication 273017; the compound ST 557 is disclosed in the Italian patent application 47609 A/88; the compound ST 564 is disclosed in the Italian patent application No. 47652 A/88; and the compound ST 626 is disclosed in J. Med Chem 29:1615 (1986).

The only known pharmacological activity for all these compounds is as antihypertensive agents.

SUMMARY OF THE INVENTION

The present invention relates to 6,7-disubstituted-2-aminotetralines of general formula

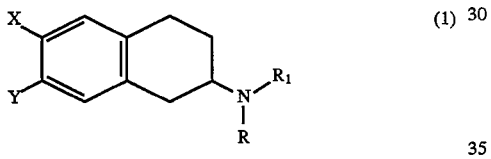

and their pharmacologically acceptable salts, wherein X and Y, identical or different, are selected from the group consisting of methoxy, acetoxy and fluoro; and R and $R_1$, identical or different, are selected from the group consisting of hydrogen, ethyl, propyl, cyclopropylmethyl, 2-hydroxy-2-phenylethyl, 2-hydroxy-2-(4-methylphenyl)ethyl and 2-hydroxy-3-(4-methoxyphenoxy)propyl.

The present invention also relates to the use of these 6,7-disubstituted-2-aminotetralines for producing pharmaceutical compositions having immunomodulating activity and the pharmaceutical compositions thus produced.

Among the 6,7-disubstituted-2-aminotetralines of formula (1), particularly preferred are the compounds wherein:

(1) X=Y=methoxy; R=hydrogen; $R_1$=2-hydroxy-(4-methylphenyl)ethyl: 2-[(N-2-hydroxy-2-(4-methylphenyl)ethyl)amino]-6,7-dimethoxytetraline. (hereinbelow: ST 563);

(2) X=Y=methoxy; R=ethyl, $R_1$=2-hydroxy-2-phenylethyl: 2-[(N-ethyl, N-2-hydroxy-2-phenylethyl)amino]-6,7-dimethoxytetraline. (hereinbelow: ST 570);

(3) X=Y=methoxy; R=$R_1$=cyclopropylmethyl: 2-[(N,N-dicyclopropylmethyl)amino]-6,7-dimethoxytetraline. (hereinbelow: ST 557);

(4) X=Y=methoxy; R=hydrogen, $R_1$=2-hydroxy-3-(4-methoxyphenoxy)propyl: 2-[(N-2-hydroxy-3-(4-methoxyphenoxy)propyl)amino]-6,7-dimethoxytetraline. (hereinbelow: ST 564);

(5) X=fluoro, Y=methoxy; R=$R_1$=hydrogen: 2-amino-6-fluoro-7-methoxytetraline. (hereinbelow: ST 626); and (6) X=Y=acetoxy; R=hydrogen, $R_1$=propyl: 2-N-propylamino-6,7-diacetoxytetraline. (hereinbelow: ST 608).

DETAILED DESCRIPTION OF THE INVENTION

The present invention relates to 6,7-disubstituted-2-aminotetralines of general formula (1)

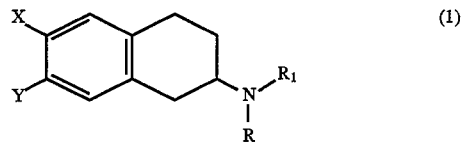

and their pharmacologically acceptable salts, wherein X and Y, identical or different, are selected from the group consisting of methoxy, acetoxy and fluoro; and R and $R_1$, identical or different, are selected from the group consisting of hydrogen, ethyl, propyl, cyclopropylmethyl, 2-hydroxy-2-phenylethyl, 2-hydroxy-2-(4-methylphenyl)ethyl and 2-hydroxy-3-(4-methoxyphenoxy)propyl.

The present invention also relates to the use of these 6,7-disubstituted-2-aminotetralines for producing pharmaceutical compositions having immunomodulating activity and the pharmaceutical compositions thus produced.

Among the 6,7-disubstituted-2-aminotetralines of formula (1), particularly preferred are the compounds wherein:

(1) X=Y=methoxy; R=hydrogen; $R_1$=2-hydroxy-(4-methylphenyl)ethyl: 2-[(N-2-hydroxy-2-(4-methylphenyl)ethyl)amino]-6,7-dimethoxytetraline. (hereinbelow: ST 563);

(2) X=Y=methoxy; R=ethyl, $R_1$=2-hydroxy-2-phenylethyl: 2-[(N-ethyl, N-2-hydroxy-2-phenylethyl)amino]-6,7-dimethoxytetraline. (hereinbelow: ST 570);

(3) X=Y=methoxy; R=$R_1$=cyclopropylmethyl: 2-[(N,N-dicyclopropylmethyl)amino]-6,7-dimethoxytetraline. (hereinbelow: ST 557);

(4) X=Y=methoxy; R=hydrogen, $R_1$=2-hydroxy-3-(4-methoxyphenoxy)propyl: 2-[(N-2-hydroxy-3-(4-methoxyphenoxy)propyl)amino]-6,7-dimethoxytetraline. (hereinbelow: ST 564);

(5) X=fluoro, Y=methoxy; R=$R_1$=hydrogen: 2-amino-6-fluoro-7-methoxytetraline. (hereinbelow: ST 626); and (6) X=Y=acetoxy; R=hydrogen, $R_1$=propyl: 2-N-propylamino-6,7-diacetoxytetraline. (hereinbelow: ST 608).

The compound ST 608 has never been previously disclosed. It can be prepared as hydrochloride, as outlined in the following reaction scheme:

Preparation of 2-(N-propyl)amino-6,7-diacetoxytetraline hydrochloride (ST 608)

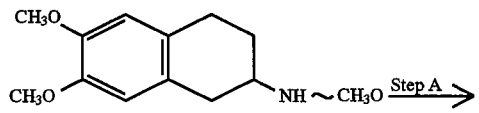

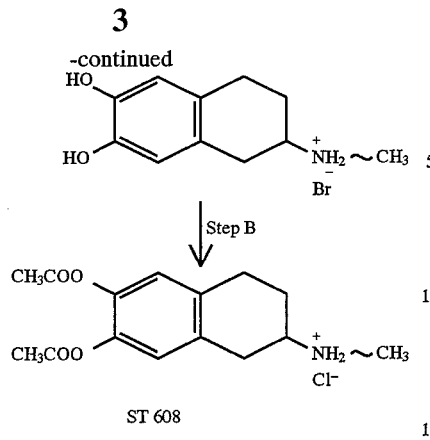

ST 608

STEP A

Preparation of 2-(N-propyl)amino-6,7-dihydroxytetraline hydrochloride 2-(N-propyl)amino-6,7 dimethoxy tetraline (prepared as described in Example 2 of the Italian patent 48779 A/86-23/12/1986) (6.6 g; 0.026 moles) were dissolved in 33 ml of 47% HBr and the resulting solution was kept at the reflux temperature overnight. Subsequently the solution was concentrated under vacuum and the residue was repeatedly washed with acetone to eliminate the excess amount of bromide acid. 8 g of a solid residue was obtained that was used as such in the following step.

STEP B

Preparation of 2-(N-propyl)amino-6,7-diacetoxy tetraline chloride ST 608

The solid of the previous step (8 g; 0.026 moles) was dissolved in 50 ml $CF_3COOH$. Acetyl chloride (40 ml; 0.56 moles) was added to the solution. The solution was kept under stirring for 48 hours at room temperature and then concentrated under vacuum. The oily residue thus obtained was dissolved in methylene chloride. The organic phase was washed several times with 5% $NaHCO_3$ solution and with $H_2O$, subsequently dried on anhydrous $Na_2SO_4$ and then concentrated under vacuum. The oily residue thus obtained was dissolved in ethyl acetate. To the solution kept at 0° C., gaseous HCl was added till saturation. A white solid precipitated that was filtered and washed with ethyl ether. 7.1 g of product was obtained. Yield 81%.

M.P.: 209–211° C.
E.A. $C_{17}H_{24}ClNO_4$

|  | C | H | N | Cl |
|---|---|---|---|---|
| calc. | 57.88 | 6.8 | 3.91 | 10.07 |
| found | 58.00 | 7.2 | 3.72 | 10.39 |

NMRD₂O δ7.1(2H, m, aromatic); 3.7–3.3(3H, m, CH—N—CH₂); 3.4–2.8(4H, m, CH₂-C=C-CH₂) 2.3(6H, s, 2CH₃COO); 2.0–1.5(4H, m, CH(H)(H); CH₂CH₃); 1.0(3H, m, CH₂C<u>H</u>₃).

The biologic activity of the compounds of the present invention was assessed via several pharmacological tests. Some of these tests are outlined hereinbelow.

TEST 1

Assessment of the "in vitro-ex vivo" effect of ST 557, ST 563, ST 570 and ST 626 on the cytotoxic activity of peritoneal macrophases (M)

Male hybrid $B_6D_2F_1$ aged 7–9 weeks and male inbred mice C57B16 aged 8 weeks were used (4 animals/group).

All the compounds were administered i.p. (25 mg/kg/day). ST 557 was also administered per os (100 mg/kg/day) from day −5 to day −1 (peritoneal exudate cell [PEC] harvesting at day 0).

PEG were obtained from sacrificed animals, 24 hours following the end of treatment, via repeated washings of the abdominal cavity. The peritoneal exudates obtained from each group of animals were pooled.

The macrophage percentage was assessed by counting in a Burker chamber; cell suspensions (concentration=$2\times10^6$ M/ml) were prepared.

The macrophage cytotoxic activity was assessed using the following two tumor cell lines as targets: Daudi, derived from a human lymphoblastoma and CEM-CM3, derived from human lymphoblastic leukemia (both lines are disclosed in ATCC—American Type Culture Collection—Cell lines of hybridoma, 5th Ed.—1985).

The experimental procedure is substantially the same as that described by Herscowitz, H. B. (1981)—Manual of Macrophage Methodology. Dekker M., Editor.

In particular, samples of cell lines were labelled with $^3$H-TdR (tritiated thymidine) and their concentration was adjusted to $5\times10^4$ cells/ml. They were then added to the macrophage preparations (using 96-well microtiter plates) and the volumes were adjusted so as to obtain Effector (macrophage)/Target (tumor cell) ratios of 20:1; 40:1 and 80:1 in an overall volume of 0.3 ml/well.

Three replicates for each sample were prepared; after 48 and 72 hours of incubation at 37° C. in 5% $CO_2$. Aliquots of 0.1 ml of supernatant were drawn out from each well and counted in a β-counter.

The macrophage cytotoxic activity results in a tumor cell lysis that causes the release of the radioactivity incorporated by the cells into the supernatant.

Based on the β-counter data (in cpm) this activity is expressed as the percentage of radioactivity released following lysis with respect to the radioactivity incorporated by the tumor cells.

The relevant formulas are as follows:

$$\% \text{ lysis after 48 hours} = \frac{48 \text{ hours sample } cpm}{\text{Total } cpm} \times 100$$

$$\% \text{ lysis after 72 hours} = \frac{72 \text{ hours sample } cpm \times 2^* + 48 \text{ hrs sample } cpm}{\text{Total } cpm \times 3^*} \times 100$$

*The multipliers account for the volume variations of the well content during the sequential samplings at the 48th hour and the 72nd hour.

The measures carried out on the samples account for a certain degree of lysis occurring spontaneously in cultured tumor cells not exposed to macrophages. Total radioactivity incorporated by the tumor cells is calculated by conducting a lysis with 1% SDS in distilled water.

As shown in the following tables 1 through 4, the tested compounds are effective in enhancing the cytotoxic activity of murine peritoneal macrophages of treated mice.

TABLE 1

"In vitro-ex vivo" ST 557 effect on murine ($B_6D_2F_1$) peritoneal macrophage cytotoxicity against a tumor target.

| | % LYSIS OF TUMOR TARGET AT: | | | | | |
|---|---|---|---|---|---|---|
| | 48 hours | | | 72 hours | | |
| TREATMENT | 20:1[a] | 40:1[a] | 80:1[a] | 20:1[a] | 40:1[a] | 80:1[a] |
| Control | 7.3 ± 0.4 | 13.8 ± 0.9 | n.d. | 9.7 ± 0.3 | 16.0 ± 2.1 | n.d. |
| 25 mg/kg/day i.p. | 10.7 ± 0.2 | 24.6 ± 0.8 | n.d. | 13.1 ± 0.3 | 29.3 ± 0.9 | n.d. |
| Control[b c] | 8.3 ± 0.6 | 9.4 ± 0.9 | 14.5 ± 0.8 | 10.2 ± 0.6 | 11.7 ± 1.3 | 18.1 ± 0.9 |
| 25 mg/kg/day i.p. | 10.8 ± 0.6 | 16.4 ± 0.8 | 28.3 ± 0.5 | 11.9 ± 0.7 | 17.9 ± 0.4 | 30.9 ± 0.1 |
| Control[b] | 5.9 ± 0.4 | 6.0 ± 0.1 | 6.3 ± 0.4 | 10.6 ± 0.5 | 11.2 ± 0.6 | 11.0 ± 0.7 |
| 25 mg/kg/day i.p. | 7.8 ± 0.7 | 13.2 ± 0.7 | 32.4 ± 0.9 | 13.0 ± 0.7 | 18.7 ± 0.9 | 45.3 ± 0.9 |
| Control | 22.0 ± 0.9 | 23.5 ± 0.8 | 26.4 ± 0.5 | 32.4 ± 1.0 | 37.5 ± 1.4 | 40.5 ± 0.6 |
| 100 mg/kg/day os | 22.7 ± 0.6 | 30.1 ± 0.7 | 29.7 ± 0.9 | 29.7 ± 51.2 | 41.5 ± 1.3 | 44.4 ± 0.3 |

[a] = Effector/Target ratio
[b] = repeated experiment to confirm activity
[c] = experiment with C57B16 mice
n.d. = not determined
Control = Macrophages from PEC of untreated animals.

TABLE 2

"In vitro-ex vivo" ST 563 effect on murine ($B_6D_2F_1$) peritoneal macrophage cytotoxicity against a tumor target.

| | % OF LYSIS OF TUMOR TARGET AT: | | | | | |
|---|---|---|---|---|---|---|
| | 48 hours | | | 72 hours | | |
| TREATMENT | 20:1[a] | 40:1[a] | 80:1[a] | 20:1[a] | 40:1[a] | 80:1[a] |
| Control | 7.3 ± 0.4 | 13.8 ± 0.9 | n.d. | 9.7 ± 0.3 | 16.0 ± 2.1 | n.d. |
| 25 mg/kg/day i.p. | 9.7 ± 0.2 | 15.4 ± 0.2 | n.d. | 11.0 ±0.1 | 18.3 ± 0.1 | n.d. |
| Control[b] | 5.9 ± 0.4 | 6.0 ± 0.1 | 6.3 ± 0.4 | 10.6 ± 0.5 | 11.2 ± 0.6 | 11.0 ± 0.7 |
| 25 mg/kg/day i.p. | 7.7 ± 0.6 | 9.4 ± 0.7 | 16.0 ± 1.0 | 12.7 ± 0.5 | 14.9 ± 0.9 | 22.2 ± 1.4 |

[a] = Effector/Target ratio
[b] = repeated experiment to confirm activity
n.d. = not determined
Control = Macrophages from PEC of untreated animals.

TABLE 3

"In vitro-ex vivo" ST 570 effect on murine ($B_6D_2F_1$) peritoneal macrophage cytotoxicity against a tumor target.

| | % LYSIS OF TUMOR TARGET AT: | | | | | |
|---|---|---|---|---|---|---|
| | 48 hours | | | 72 hours | | |
| TREATMENT | 20:1[a] | 40:1[a] | 80:1[a] | 20:1[a] | 40:1[a] | 80:1[a] |
| Control | 6.3 ± 0.1 | 6.4 ± 0.4 | n.d. | 10.4 ± 0.2 | 13.0 ± 0.6 | n.d. |
| 25 mg/kg/day i.p. | 14.0 ± 0.7 | 34.7 ± 1.2 | n.d. | 19.3 ± 0.7 | 45.4 ± 2.1 | n.d. |
| Control | 8.3 ± 0.6 | 9.4 ± 0.9 | 14.5 ± 0.8 | 10.2 ± 0.6 | 11.7 ± 1.3 | 18.1 ± 0.9 |
| 25 mg/kg/day i.p.[b c] | 8.8 ± 1.2 | 13.0 ± 0.5 | 14.6 ± 0.6 | 10.8 ± 1.5 | 14.9 ± 0.3 | 16.2 ± 0.8 |
| Control | 5.9 ± 0.4 | 6.0 ± 01 | 6.3 ± 0.4 | 10.6 ± 0.5 | 11.2 ± 0.6 | 11.0 ± 0.7 |
| 25 mg/kg/day i.p.[b] | 9.0 ± 0.4 | 10.9 ± 1.0 | 19.0 ± 1.0 | 13.2 ± 0.2 | 15.7 ± 0.8 | 25.3 ± 1.0 |

[a] = Effector/Target ratio
[b] = repeated experiment to confirm activity
[c] = experiment with C57B16 mice
n.d. = not determined
Control = Macrophages from PEC of untreated animals.

TABLE 4

"In vitro-ex vivo" ST 626 effect on murine ($B_6D_2F_1$) peritoneal macrophage cytotoxicity against a tumor target.

| | % LYSIS OF TUMOR TARGET AT: | | | | | |
|---|---|---|---|---|---|---|
| | 48 hours | | | 72 hours | | |
| TREATMENT | 20:1[a] | 40:1[a] | 80:1[a] | 20:1[a] | 40:1[a] | 80:1[a] |
| Control | 6.3 ± 0.1 | 6.4 ± 0.4 | n.d. | 10.4 ± 0.2 | 13.0 ± 0.6 | n.d. |
| 25 mg/kg/day i.p. | 7.4 ± 0.2 | 12.8 ± 0.6 | n.d. | 10.8 ± 0.3 | 17.6 ± 0.8 | n.d. |
| Control | 8.3 ± 0.6 | 9.4 ± 0.9 | n.d. | 10.2 ± 0.6 | 11.7 ± 1.3 | n.d. |
| 25 mg/kg/day i.p.[b c] | 11.8 ± 0.6 | 12.7 ± 0.1 | n.d. | 12.6 ± 0.1 | 13.5 ± 0.7 | n.d. |
| Control | n.d. | 11.7 ± 0.2 | 12.0 ± 0.3 | n.d. | 18.7 ± 2.1 | 20.5 ± 0.9 |
| 25 mg/kg/day i.p.[b] | n.d. | 18.7 ± 0.1 | 18.8 ± 0.1 | n.d. | 27.5 ± 0.6 | 28.0 ± 0.7 |
| Control | 5.9 ± 0.4 | 6.0 ± 0.1 | 6.3 ± 0.4 | 10.6 ± 0.5 | 11.2 ± 0.6 | 11.0 ± 0.7 |
| 25 mg/kg/day i.p.[b] | 8.0 ± 0.8 | 11.6 ± 0.7 | 28.0 ± 5.6 | 12.3 ± 0.6 | 14.3 ± 0.6 | 32.0 ± 4.3 |

[a] = Effector/Target ratio
[b] = repeated experiment to confirm activity
[c] = experiment with C57B16 mice
n.d. = not determined
Control = Macrophages from PEC of untreated animals.

TEST 2

Assessment of the "in vitro-ex vivo" effect of ST 557, ST 563, ST 564, ST 570, ST 608 and ST 626 on the phagocytic activity of exudate peritoneal cells (PEC)

Male $B_6D_2F_1$ mice aged 6–8 weeks (5 animals each group) were used.

The compounds were administered i.p. (25 mg/kg/day), ST 557, ST 563 and ST 626 were also administered per os (100 mg/kg/day) from day −5 to day −1 (PEC harvesting at day 0).

The experimental procedure was substantially the same as that described by Williams et al., in "Methods in Immunology and Immunochemistry", Acad. Press. 5:261 (1976).

In particular, 24 hours following the end of the treatment, PECs from each experimental group were harvested, pooled and their concentration was adjusted to $4 \times 10^6$ cells/ml.

To volumes of 250 μl of each PEC sample were added equal volumes of 0.4% SRBC (Sheep Red Blood Cells) opsonized with hyperimmune serum.

The samples (duplicate) were incubated for 1 hour and then subjected to hypotonic shock in order to remove the non-phagocytized SRBC. After restoring the osmolarity, the phagocytes were cytocentrifuged, stained with a differential dye and observed under the microscope.

The results were expressed as:
(a) percentage of cells that have phagocytized with respect to 100 phagocytizing cells;
(b) total number of phagocytized SRBC;
(c) average number of SRBC in each phagocyte.

As shown in the following tables 5 through 10, the tested compounds markedly enhance PEC phagocytic activity.

TABLE 5

SRBC phagocytosis by murine ($B_6D_2F_1$) PEC following ST 557 administration.

| TREATMENT | Fagocytizing cells[a] % | Total n° SRBC phagocytized[b] | SRBC per phagocytizing cell[c] |
|---|---|---|---|
| Control | 27.5 | 67.0 | 2.10 |
| 25 mg/kg/day i.p. | 29.5 | 93.5 | 3.20 |

TABLE 5-continued

SRBC phagocytosis by murine ($B_6D_2F_1$) PEC following ST 557 administration.

| TREATMENT | Fagocytizing cells[a] % | Total n° SRBC phagocytized[b] | SRBC per phagocytizing cell[c] |
|---|---|---|---|
| Control | 44.5 | 107.5 | 2.42 |
| 100 mg/kg/day os | 59.0 | 190.5 | 3.23 |

[a] = percentage of cells that have phagocytized with respect to 100 phagocytizing cells.
Mean value of 5 pooled samples, examined in duplicate.
[b] = total SRBC phagocytized by "a".
[c] = average number of SRBC in each phagocyte
Control = PEC of untreated animals.

TABLE 6

SRBC phagocytosis by murine ($B_6D_2F_1$) PEC following ST 563 administration.

| TREATMENT | Fagocytizing cells[a] % | Total n° SRBC phagocytized[b] | SRBC per phagocytizing cell[c] |
|---|---|---|---|
| Control | 27.5 | 57.0 | 2.10 |
| 25 mg/kg/day i.p. | 42.5 | 146.0 | 3.40 |
| Control | 44.5 | 107.5 | 2.42 |
| 100 mg/kg/day os | 58.5 | 164.0 | 2.80 |

[a] = percentage of cells that have phagocytized with respect to 100 phagocytizing cells.
Mean value of 5 pooled samples, examined in duplicate.
[b] = total number of SRBC phagocytized by "a".
[c] = average number of SRBC in each phagocyte
Control = PEC of untreated animals.

TABLE 7

SRBC phagocytosis by murine ($B_6D_2F_1$)
PEC following ST 564 administration.

| TREATMENT | Fagocytizing cells[a] % | Total n° SRBC phagocytized[b] | SRBC per phagocytizing cell[c] |
|---|---|---|---|
| Control | 27.5 | 57.0 | 2.1 |
| 25 mg/kg/day i.p. | 40.0 | 126.5 | 3.2 |

[a] = percentage of cells that have phagocytized with respect to 100 phagocytizing cells.
Mean value of 5 pooled samples, examined in duplicate.
[b] = total number of SRBC phagocytized by "a".
[c] = average number of SRBC in each phagocyte
Control = PEC of untreated animals.

TABLE 8

SRBC phagocylosis by murine ($B_6D_2F_1$)
PEC following ST 570 administration.

| TREATMENT | Fagocytizing cells[a] % | Total n° SRBC phagocytized[b] | SRBC per phagocytizing cell[c] |
|---|---|---|---|
| Control | 45.4 | 96.5 | 2.1 |
| 25 mg/kg/day i.p. | 41.0 | 137.5 | 3.3 |

[a] = percentage of cells that have phagocytized with respect to 100 phagocytizing cells.
Mean value of 5 pooled samples, examined in duplicate;
[b] = total number of SRBC phagocytized by "a".
[c] = average number of SRBC in each phagocyte;
Control = PEC of untreated animals.

TABLE 9

SRBC phagocytosis by murine ($B_6D_2F_1$)
PEC following ST 608 administration.

| TREATMENT | Fagocytizing cells[a] % | Total n° SRBC phagocytized[b] | SRBC per phagocytizing cell[c] |
|---|---|---|---|
| Control | 45.4 | 96.5 | 2.10 |
| 25 mg/kg/day i.p. | 41.0 | 137.5 | 3.30 |

[a] = percentage of cells that have phagocytized with respect to 100 phagocytizing cells.
Mean value of 5 pooled samples, examined in duplicate.
[b] = total number of SRBC phagocytized by "a".
[c] = average number of SRBC in each phagocyte.
Control = PEC of untreated animals.

TABLE 10

SRBC phagocytosis by murine ($B_6D_2F_1$)
PEC following ST 626 administration.

| TREATMENT | Fagocytizing cells[a] % | Total n° SRBC phagocytized[b] | SRBC per phagocytizing cell[c] |
|---|---|---|---|
| Control | 45.4 | 96.5 | 2.10 |
| 25 mg/kg/day i.p. | 41.0 | 137.5 | 3.30 |
| Control | 44.5 | 107.5 | 2.42 |
| 100 mg/kg/day os | 57.0 | 222.0 | 3.89 |

[a] = Percentage of cells that have phagocytized with respect to 100 phagocytizing cells.
Mean value of 5 pooled samples, examined in duplicate.
[b] = total number of SRBC phagocytized by "a".
[c] = average number of SRBC in each phagocyte.
Control = PEC of untreated animals.

TEST 3

Assessment of the "in vitro-ex vivo" effect of ST 557, ST 563 and ST 570 on the cytostatic activity of peritoneal macrophages Male $B_6D_2F_1$ mice aged 7–9 weeks (5 animals per group) were used.

The compounds were administered i.p. (25 mg/kg/day), ST 557 and ST 563 were also administered per os (100 mg/kg/day) from day −5 to day −1 (peritoneal cell harvesting at day 0).

The macrophages and target tumor cell lines were prepared as in test 1 and their concentrations were adjusted to $1 \times 10^6$ M/ml and $5 \times 10^4$ cell/ml, respectively.

Volumes of tumor cells were added to the macrophage preparations so as to obtain Effector/Target ratios of 10:1, 20:1 and 40:1.

Each sample was pulsed with $^3$H-TdR for 18 hours in order to label the tumor cells, which were then collected on filters and counted in a beta-counter.

The macrophage cytostatic activity is expressed as percentage inhibition of tumor cell replication, by assessing the radioactivity incorporated by the tumor cells in each sample with respect to the maximum radioactivity incorporated by a sample consisting of tumor cells only.

$$\% \text{ of cytostasis} = 100 - \frac{\text{sample } cpm}{\text{total } cpm} \times 100$$

As shown in the following tables 11 through 13, the tested compounds are effective in enhancing the cytostatic activity of peritoneal macrophages of treated mice.

TABLE 11

"In vitro-ex vivo" ST 557 effect on the cytostatic activity of peritoneal macrophages of treated mice.

| | % of inhibition of target tumor growth at the following E/T ratios: | | |
|---|---|---|---|
| TREATMENT | 10:1 | 20:1 | 40.1 |
| Control | n.d. | 31.7 ± 2.6 | 53.5 ± 1.6 |
| 25 mg/kg/day i.p. | n.d. | 45.1 ± 1.1 | 68.9 ± 1.4 |
| Control | 12.3 ± 1.5 | 28.6 ± 4.8 | 40.1 ± 7.9 |
| 100 mg/kg/day os | 24.3 ± 2.2 | 38.7 ± 1.6 | 62.8 ± 3.1 |

Control = PEC macrophages of untreated mice.

TABLE 12

"In vitro-ex vivo" ST 563 effect on the cytostatic activity of peritoneal macrophages of treated mice.

| | % of inhibition of target tumor growth at the following E/T ratios: | | |
|---|---|---|---|
| TREATMENT | 10:1 | 20:1 | 40.1 |
| Control | n.d. | 31.7 ± 2.6 | 53.5 ± 1.6 |
| 25 mg/kg/day i.p. | n.d. | 35.0 ± 1.6 | 55.7 ± 1.4 |
| Control | 12.3 ± 1.5 | 28.6 ± 4.8 | 40.1 ± 7.9 |
| 100 mg/kg/day os | 25.0 ± 4.9 | 47.3 ± 0.6 | 62.8 ± 3.1 |

Control = PEC macrophages of untreated mice.

TABLE 13

"In vitro-ex vivo" ST 570 effect on the cytostatic activity of peritoneal macrophages of treated mice.

| TREATMENT | % of inhibition of target tumor growth at the following E/T ratios: | | |
|---|---|---|---|
|  | 10:1 | 20:1 | 40.1 |
| Control | n.d. | 31.7 ± 2.6 | 53.5 ± 1.6 |
| 25 mg/kg/day i.p. | n.d. | 38.3 ± 2.5 | 71.0 ± 2.4 |

Control = PEC macrophages of untreated mice.

TEST 4

Assessment of the "in vitro-ex vivo" effect of ST 557, ST 563, ST 608 on the mytogen (PHA, LPS)-induced splenocyte proliferation in mice Male $B_6D_2F_1$ mice aged 6–10 weeks (4 animals per group) were used.

The compounds were administered i.p. 25 mg/kg/day, from day −5 to −1 (spleen excision at day 0).

PHA (active on T lymphocytes) and LPS (active on B lymphocytes) were used as mytogens. Each mytogen was tested at three different concentrations (suboptimal, optimal, superoptimal): 0.5, 4 and 6 mcg/ml/well and 0.5, 150 and 500 mcg/ml/well, respectively.

The experimental procedure was conducted substantially as described by Kirchner et al., "Splenic suppressor macrophages induced in mice by injection of C. parvum", J. Immunol., 1975, 115: 1212.

In particular, the cell suspensions obtained from the spleens of the animals of the same group were pooled and the cell concentration was adjusted to $5 \times 10^6$ cells/ml.

To volumes of 0.1 ml of each sample, equal volumes of the mytogen preparations were added so as to obtain, for each mytogen, the previously indicated final concentrations.

Each sample was prepared in triplicate in U-bottom microtiters. A control, to which 0.1 ml of medium were added instead of the mytogen, was also prepared. The control permits the extent of spontaneous proliferation in the absence of stimulation to be assessed.

The samples were incubated at 37° C. for 48 hours and then they were pulsed with 20 µl $^3$H-TdR (25 µCi/ml).

After 18 hours of further incubation, the cells were collected on filters and counted in a beta-counter.

The results of each sample are expressed by calculating the value of the area under the curve (AUC) obtained by plotting the values of the incorporated radioactivity (in cpm) versus the various concentrations of each mytogen.

In addition to AUC, the stimulation index (SI) is also considered, that is defined as follows.

$$SI = \frac{AUC \text{ treated}}{AUC \text{ control}}$$

As shown in the following tables 14 through 16, the tested compounds are effective in enhancing the mytogen-induced splenocytes proliferation.

TABLE 14

Mytogen (PHA, LPS)-induced splenocyte proliferation in mice treated with ST 557.

| TREAT- | AUC[a] | | S.I.[b] | |
|---|---|---|---|---|
| MENT | PHA | LPS | PHA | LPS |
| Control | 164 ± 4 | 8118 ± 866 | 1.27 | 1.22 |
| 25 mg/kg/day i.p. | 200 ± 15 | 10312 ± 1253 | (1.00–1.59) | (1.10–1.34) |
| Control | 123 ± 6 | 16407 ± 895 | 1.13 | 1.15 |
| 25 mg/kg/day i.p. | 141 ± 7 | 18914 ± 389 | (1.03–1.25) | (1.07–1.24) |
| Control | 200 ± 12 | n.d. | 1.73 | n.d. |
| 25 mg/kg/day i.p. | 348 ± 15 | n.d. | (1.56–1.93) | n.d. |

[a] = Area under curve ($\times 10^{-3}$):X ± ranges of variation
[b] = Stimulation index:ranges of variation are indicated in brackets.
Control = Mytogen-induced splenocyte proliferation in untreated mice.
n.d. = Not determined.

TABLE 15

Mytogen (PHA, LPS)-induced splenocyte proliferation in mice treated with ST 563.

| TREAT- | AUC[a] | | S.I.[a] | |
|---|---|---|---|---|
| MENT | PHA | LPS | PHA | LPS |
| Control | 164 ± 4 | 8118 ± 866 | 1.09 | 1.13 |
| 25 mg/kg/day i.p. | 179 ± 3 | 9203 ± 108 | (1.05–1.13) | (0.90–1.41) |
| Control | 200 ± 12 | 26790 ± 278 | 1.28 | 0.95 |
| 25 mg/kg/day i.p. | 256 ± 21 | 25592 ± 1203 | (1.10–1.47) | (0.90–1.01) |
| Control | 123 ± 5 | 16407 ± 895 | 1.12 | 1.13 |
| 25 mg/kg/day i.p. | 139 ± 5 | 18461 ± 587 | (1.03–1.23) | (1.03–1.23) |

[a] = Area under the curve ($\times 10^{-3}$):X ± ranges of variation
[b] = Stimulation index; ranges of variation are indicated in brackets.
Control = Mytogen-induced splenocyte proliferation in untreated mice.

TABLE 16

Mytogen (PHA, LPS)-induced splenocyte proliferation in mice treated with ST 608.

| TREAT- | AUC[a] | | S.I.[a] | |
|---|---|---|---|---|
| MENT | PHA | LPS | PHA | LPS |
| Control | 164 ± 4 | 8118 ± 866 | 1.11 | 1.27 |
| 25 mg/kg/day i.p. | 183 ± 6 | 10333 ± 807 | (1.05–1.18) | (1.06–1.53) |
| Control | 123 ± 6 | 16407 ± 895 | 1.04 | 1.10 |
| 25 mg/kg/day i.p. | 128 ± 4 | 18054 ± 970 | (0.95–1.13) | (0.98–1.22) |
| Control | 136 ± 6 | 12005 ± 434 | 1.07 | 1.20 |
| 25 mg/kg/day i.p. | 146 ± 4 | 14490 ± 433 | (0.99–1.16) | (1.12–1.28) |
| Control | 206 ± 8 | 14907 ± 306 | 1.12 | 1.06 |
| 25 mg/kg/day i.p. | 233 ± 2 | 15892 ± 339 | (1.07–1.18) | (1.02–1.11) |

[a] = Area under the curve ($\times 10^{-3}$):X ± ranges of variation
[b] = Stimulation index; ranges of variation are in indicated in brackets.
Control = Mytogen-induced splenocyte proliferation in untreated mice.

TEST 5

Assessment of the "in vitro-ex vivo" effect of ST 557, ST 563 ST 564 on the mytogen (PHA, ConA, LPS)-Induced splenocyte proliferation in mice Immunodepressed with cyclophosphamide Male $B_6D_2F_1$ mice aged 7–9 weeks (5 mice per group) were used.

The immunosuppressor (cyclophosphamide) was administered i.p. at the dose of 100 mg/kg at day −5. The compounds were administered j.p. (25 mg/kg/day) and per os (100 mg/kg/day) from day −5 to day −1 (spleen excision at day 0).

Splenocyte proliferation was induced by three different mytogens: PHA and ConA active on T-lymphocytes, and LPS active on B-lymphocytes. Each mytogen was tested at three different concentrations (suboptimal, optimal and superoptimal) corresponding to 0.5, 4 and 6 mcg/ml/well for PHA; 0.5, 4 and 8 mcg/ml/well for ConA and 0.5, 150 and 500 mcg/ml/well for LPS.

The experimental procedure is identical to that described in test 4.

The results are expressed as both AUC (see test 4) and S.I. In order to assess the efficacy of the immunosuppressor and the activity of the tested compounds, S.I. has been determined both for the immunodepressed controls (with respect to the normal controls) and for the immunodepressed treated animals (with respect to the immunodepressed controls), $$SI = \frac{AUC \text{ immunodepressed controls}}{AUC \text{ normal controls}} \quad (a)$$

$$SI = \frac{AUC \text{ Immunodepressed tested animals}}{AUC \text{ Immunodepressed controls}} \quad (b)$$

As shown in the following tables 17 through 19, the tested compounds are active in enhancing the mytogen-induced splenocyte proliferation in immunodepressed mice.

TABLE 17

Mytogen (PHA, ConA, LPS)-induced splenopcyte proliferation in immunodepressed mice treated with ST 557.

| TREATMENT | AUC[a] | | | S.I.[b] | | |
|---|---|---|---|---|---|---|
| | PHA | ConA | LPS | PHA | ConA | LPS |
| Control | 214 ± 15 | 1097 ± 33 | 12168 ± 418 | 0.46 | 0.46 | 0.07 |
| Immunodepressed control | 100 ± 9 | 507 ± 22 | 923 ± 109 | (0.39–0.54) | (0.45–0.49) | (0.06–0.08) |
| Immunodepressed + ST 557 i.p.[c] | 191 ± 10 | 763 ± 14 | 5411 ± 214 | 1.90 (1.65–2.21) | 1.50 (1.41–1.60) | 5.86 (5.03–6.91) |
| Control | n.d. | 1319 ± 54 | 10968 ± 327 | n.d. | 0.55 | 0.41 |
| Immunodepressed control | n.d. | 732 ± 26 | 4599 ± 366 | (0.51–0.59) | (0.37–0.46) | |
| Immunodepressed + ST 557 os[d] | n.d. | 675 ± 27 | 4485 ± 433 | n.d. | 0.92 (0.85–0.99) | 0.97 (0.81–1.16) |

[a] = area under curve ($\times 10^{-3}$) with range of variation in brackets.
[b] = Stimulation index, with range of variation in brackets.
[c] = 25 mg/kg/day
[d] = 100 mg/kg/day
n.d. = Not determined.

TABLE 18

Mytogen (PHA, ConA, LPS)-induced splenocyte proliferation in immunodepressed mice treated with ST 563.

| TREATMENT | AUC[a] | | | S.I.[b] | | |
|---|---|---|---|---|---|---|
| | PHA | ConA | LPS | PHA | ConA | LPS |
| Control | 214 ± 15 | 1097 ± 33 | 12168 ± 418 | 0.46 | 0.46 | 0.07 |
| Immunodepressed control | 100 ± 9 | 507 ± 22 | 923 ± 109 | (0.39–0.54) | (0.45–0.49) | (0.06–0.08) |
| Immunodepressed + ST 563 i.p.[c] | 217 ± 14 | 666 ± 16 | 3715 ± 200 | 2.17 (1.86–2.54) | 1.31 (1.22–1.40) | 4.02 (3.38–4.83) |
| Control | n.d. | 1319 ± 54 | 10968 ± 327 | n.d. | 0.55 | 0.41 |
| Immunodepressed control | n.d. | 732 ± 26 | 4599 ± 366 | n.d. | (0.51–0.59) | (0.37–0.46) |
| Immunodepressed + ST 563 os[d] | n.d. | 619 ± 12 | 3501 ± 360 | n.d. | 0.84 (0.80–0.89) | 0.41 (0.63–0.91) |

[a] = Area under curve ($\times 10^{-3}$) with range of variation in brackets.
[b] = Stimulation index, with range of variation in brackets.
[c] = 25 mg/kg/day
[d] = 100 mg/kg/day
n.d. = Not determined.

TABLE 19

Mytogen (PHA, ConA, LPS)-induced splenocyte proliferation in immunodepressed mice treated with ST 564.

| TREATMENT | AUC[a] | | | S.I.[b] | | |
|---|---|---|---|---|---|---|
| | PHA | ConA | LPS | PHA | ConA | LPS |
| Control | 214 ± 15 | 1097 ± 33 | 12168 ± 418 | 0.46 | 0.46 | 0.07 |
| Immunodepressed control | 100 ± 9 | 507 ± 22 | 923 ± 109 | (0.39–0.54) | (0.45–0.49) | (0.06–0.08) |
| Immunodepressed + ST 564 i.p.[c] | 205 ± 6 | 514 ± 10 | 2533 ± 314 | 2.05 (1.82–2.32) | 1.01 (0.95–1.08) | 2.74 (2.14–3.49) |
| Control | n.d. | 1319 ± 54 | 10968 ± 327 | n.d. | 0.55 (0.51–0.59) | 0.41 (0.37–0.46) |
| Immunodepressed control | n.d. | 732 ± 26 | 4599 ± 366 | | | |
| Immunodepressed + ST 564 os[d] | n.d. | 577 ± 41 | 3023 ± 257 | n.d. | 0.78 (0.70–0.87) | 0.65 (0.55–0.77) |

[a] = Area under curve ($\times 10^{-3}$) with range of variation in brackets.
[b] = Stimulation index, with range of variation in brackets.
[c] = 25 mg/kg/day
[d] = 100 mg/kg/day
n.d. = Not determined.

Several tests have shown the low toxicity of the compounds of the present invention. Some of these tests are described below.

TOXICOLOGICAL TESTS (a) TOLERABILITY

The test was conducted in male Swiss albino mice weighing 22–24 g.

A group of animals (4 animals/dose) which had been kept fasting for 18 hours, were orally administered the compounds ST 557, ST 563, ST 564 and ST 570 dissolved in twice distilled water.

A further group of animals, which had free access to food and water, were administered intravenously the same compounds dissolved in saline at pH 7. All the animals were kept under observation for 7 days.

The test results are shown in Table 20.

(b) LD50

LD50 was determined according to Carrol S. Weil's method, Biometrics, pages 249–263 (1952) in male Swiss albino mice weighing 22–24 g.

The various compounds dissolved in 0.9% saline were administered intravenously. The results are shown in Table 21.

TABLE 20

| | TOLERABILITY doses mg/kg | |
|---|---|---|
| Compounds | os | i.v. |
| ST 563 | >50 | >20 |
| ST 557 | >20 | >4 |
| ST 570 | >50 | >20 |
| ST 564 | >50 | >20 |

TABLE 21

| Compound | LD50 mg/kg | from mg/kg | to mg/kg |
|---|---|---|---|
| ST 570 | 34.92 | 44.30 | 27.53 |
| ST 563 | 35.71 | 43.37 | 29.41 |
| ST 557 | 28.28 | 28.28 | 28.28 |
| ST 564 | 44.54 | 20.00 | 99.17 |

The dose of the compounds of formula (1) to be administered will be determined having regard to the age, weight and general conditions of the patient. Effective results can be obtained with doses of about 0.5–5 mg/kg body weight/day. Because of the low toxicity of the compounds of the present invention larger doses can be administered, such as 8–10 mg/kg body weight/day.

The compounds of the present invention can be formulated by procedures well-known to those skilled in the pharmaceutical technology into the usual administration forms which comprise orally or parenterally administrable solid and liquid unit dosage forms. These unit dosage forms comprise from about 20 to about 100 mg of active principle, in addition to the usual excipients.

What is claimed is:

1. 2-N-propylamino-6,7-diacetoxytetraline.

2. A pharmaceutical composition comprising 2-N-propylamino-6,7-diacetoxytetraline, and a pharmacologically acceptable excipient therefore.

* * * * *